(12) United States Patent
Moriyama

(10) Patent No.: US 8,100,825 B2
(45) Date of Patent: Jan. 24, 2012

(54) ENDOSCOPE AND SUPPORTIVE MEMBER FOR BENDING OPERATION OF THE SAME

(75) Inventor: Hiroki Moriyama, Akishima (JP)

(73) Assignee: Olympus Corporation (JP)

( * ) Notice: Subject to any disclaimer, the term of this patent is extended or adjusted under 35 U.S.C. 154(b) by 910 days.

(21) Appl. No.: 11/570,879

(22) Filed: Dec. 18, 2006

(65) Prior Publication Data

US 2008/0119696 A1 May 22, 2008

Related U.S. Application Data

(63) Continuation of application No. PCT/JP2005/011126, filed on Jun. 17, 2005.

(30) Foreign Application Priority Data

Jun. 17, 2004 (JP) .................................. 2004-180190

(51) Int. Cl.
*A61B 1/00* (2006.01)

(52) U.S. Cl. ........................................ 600/146; 600/149

(58) Field of Classification Search .......... 600/146–147, 600/148–149
See application file for complete search history.

(56) References Cited

U.S. PATENT DOCUMENTS

| | | | | |
|---|---|---|---|---|
| 4,207,873 A | * | 6/1980 | Kruy | 600/146 |
| 4,461,282 A | * | 7/1984 | Ouchi et al. | 600/148 |
| 5,007,406 A | * | 4/1991 | Takahashi et al. | 600/119 |
| 5,993,381 A | * | 11/1999 | Ito | 600/131 |
| 6,638,213 B2 | * | 10/2003 | Ogura et al. | 600/148 |
| 2001/0034472 A1 | * | 10/2001 | Fujii et al. | 600/146 |
| 2002/0062063 A1 | | 5/2002 | Ogura et al. | |

FOREIGN PATENT DOCUMENTS

| | | |
|---|---|---|
| JP | 2-141401 | 11/1990 |
| JP | 2005-245545 | 9/2005 |
| KR | 1020020038662 | 5/2002 |

OTHER PUBLICATIONS

Korean Notice of Allowance dated Dec. 18, 2008.
English translation of Chinese Patent Office Action dated May 9, 2008 corresponding to Chinese Patent Application No. 200580019275.9.

(Continued)

*Primary Examiner* — Anhtuan Nguyen
*Assistant Examiner* — Alireza Nia
(74) *Attorney, Agent, or Firm* — Ostrolenk Faber LLP

(57) ABSTRACT

An endoscope includes an insertion portion having a bendable portion; an operation portion from which the insertion portion extends; a first bending operation knob arranged on a surface of the operation portion and including depressions and first protrusions, to bend the bendable portion in a first direction when rotated; and a second bending operation knob arranged over the first bending operation knob and including depressions and second protrusions, to bend the bendable portion in a second direction when rotated. A length of the second protrusion from a center of rotation to a tip portion is longer than a length of the first protrusion from the center of rotation to tip portions of the first protrusions, and the second protrusion has a depression near a projection of a circular orbit of rotation of each tip portion of the first protrusions onto a surface facing the first bending operation knob.

5 Claims, 7 Drawing Sheets

OTHER PUBLICATIONS

Japanese Patent Laid-open Publication No. SHO 62-32932, "Bending Device of Endoscope", Asahi Optical Co., Ltd., published Feb. 12, 1987 (English abstract enclosed).

Japanese Utility Model Publication No. HEI 02-141401, "Endoscope", Fuji Photo Optical Co., Ltd., Nov. 28, 1990 (English abstract enclosed).

PCT/JP2005/011126 International Search Report dated Sep. 6, 2005 (English translation thereof enclosed herewith).

Search Report issued by European Patent Office in connection with corresponding application No. EP 05 75 1584 on Oct. 5, 2010.

* cited by examiner

ENDOSCOPE AND SUPPORTIVE MEMBER FOR BENDING OPERATION OF THE SAME

CROSS-REFERENCE TO RELATED APPLICATIONS

This application is a continuation of PCT international application Ser. No. PCT/JP2005/011126 filed Jun. 17, 2005 which designates the United States, incorporated herein by reference, and which claims the benefit of priority from Japanese Patent Application No. 2004-180190, filed Jun. 17, 2004, incorporated herein by reference.

BACKGROUND OF THE INVENTION

1. Field of the Invention

The present invention relates to an endoscope and a supportive member for bending operation of the endoscope, and more particularly to an endoscope in which a bending operation knob is provided and a supportive member for bending operation of the endoscope.

2. Description of the Related Art

Conventionally, endoscopes are widely utilized for observations and various kinds of treatments of examined regions inside body cavities and the like. The endoscope has an elongated insertion portion which can be inserted inside the body cavities.

The endoscope, which is provided with a flexible insertion portion, generally includes a bendable portion. The bendable portion is a distal end part of the insertion portion, and bending pieces are housed therein. A traction member such as a bending wire penetrates through the insertion portion of the endoscope. The bending wire is connected to the bending piece in the bendable portion. Further, a pair of bending operation knobs is provided in an operation portion connected to the proximal end of the insertion portion of the endoscope. An operator rotates the pair of bending operation knobs to pull and/or loosen the bending wire. According to the operation by the operator, the bendable portion of the endoscope bends in a desired direction, i.e., up, down, to the left, and to the right. There are two bending operation knobs in the operation portion, one for upward and downward bending and another for rightward and leftward bending. The operator selects and rotates one of the two bending operation knobs as appropriate to bend the bendable portion at a desired angle. Thus, the operator can easily observe the examined region by directing an observation optical system arranged at a distal end portion of the insertion portion toward a target direction. In addition, the operator can easily insert the insertion portion of the endoscope into the examined region.

For example, Japanese Patent Application Laid-Open No. 62-32932 describes an endoscope which has a pair of bending operation knobs provided in an operation portion for bending the insertion portion of the endoscope in upward and downward directions and rightward and leftward directions.

However, when the endoscope is employed in medical field, e.g., when the operator inserts the insertion portion of the endoscope into a large intestine, which is a body cavity of a patient, peristaltic movements of the large intestine sometimes works to push the insertion portion towards an anus side and out of the large intestine. Therefore, the operator has to push the insertion portion of the endoscope into the large intestine by holding the insertion portion by one hand while holding the operation portion of the endoscope by another hand. In addition, when the distal end portion of the endoscope reaches a curved portion, such as a sigmoid colon, in the large intestine, the operator needs to direct the distal end portion of the endoscope in a desired direction of insertion by bending the bendable portion of the endoscope in order to facilitate the farther insertion. For bending the bendable portion, the operator manipulates the bending operation knobs in the operation portion with the hand that holds the operation portion of the endoscope, thereby bending the bendable portion to direct the distal end portion of the endoscope in a direction along the curve of the large intestine, while pushing the insertion portion of the endoscope into the large intestine with the other hand.

Further, when the operator directs the distal end portion of the endoscope toward a desired direction for the observation of the examined region inside the body cavity of the patient after the distal end portion reaches the examined region, the operator is required to hold the insertion portion of the endoscope with the other hand in order to prevent the peristaltic movements of the large intestine, for example, from pushing back the insertion portion of the endoscope towards the anus side. Therefore, in some cases as described above, the operator needs to manipulate a pair of bending operation knobs by one hand in order to bend and direct the distal end portion of the endoscope upward, downward, rightward, and/or leftward.

The operator should to be highly skilled to direct the distal end portion of the endoscope toward a desired direction while manipulating the pair of bending operation knobs with one hand. Meanwhile, the size of the hand varies from one operator to another, and the number of female medical doctors, who are expected to have relatively small hands, increases. For medical doctors with small hands, it is not easy to adjust the direction of the bendable portion of the endoscope in four directions, in other words, it is not easy to manipulate two bending operation knobs simultaneously in order to bend the bendable portion in rightward/leftward or upward/downward.

In electronic endoscope systems, the upward/downward directions mentioned above correspond to upward/downward directions on a screen of a monitor, and a picture moves on the screen according to the bending operation. During the bending operation, the operator generally performs upward/downward bending operations more frequently than rightward/leftward bending operations by rotating the knobs and bending the bendable portion of the endoscope upward/downward on the screen of the monitor. Therefore, in general endoscopes, the upward/downward bending operation knob is generally arranged closer to the operation portion.

SUMMARY OF THE INVENTION

According to an aspect of the present invention, an endoscope includes an insertion portion having a bendable portion; an operation portion from which the insertion portion extends; a first bending operation knob arranged on a surface of the operation portion and including plural depressions and plural first protrusions, to bend the bendable portion in a first direction when rotated; and a second bending operation knob arranged over the first bending operation knob and including plural depressions and plural second protrusions, to bend the bendable portion in a second direction when rotated. A length of one of the plural second protrusions from a center of rotation to a tip portion is longer than a length of one of the plural first protrusions from the center of rotation to tip portions of the plural first protrusions, and at least one of the plural second protrusions has a depression near a projection of a circular orbit of rotation of each tip portion of the plural first protrusions onto a surface facing the first bending operation knob.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention will be described below with reference to the accompanying drawings. It should be noted that the present invention is not limited to the embodiments described below.

Figure 1:
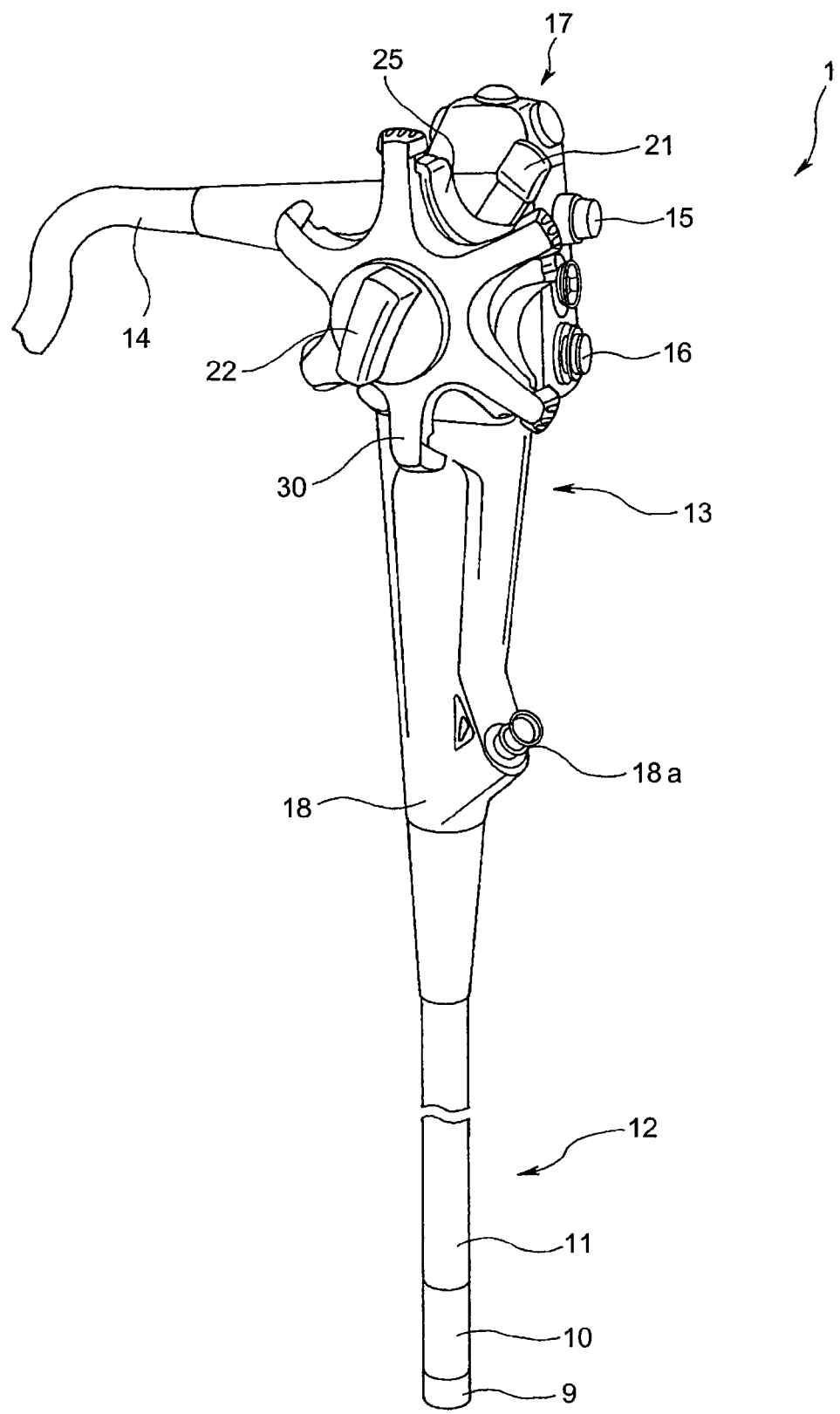
FIG. 1 shows a schematic structure of an endoscope according to a first embodiment.

FIGS. 1 to 4 show a structure of an endoscope according to a first embodiment of the present invention. FIG. 1 is a schematic view of a schematic structure of the endoscope of the present invention. As shown in FIG. 1, an endoscope 1 of the first embodiment mainly includes an operation portion 13 in which various kinds of operation levers are provided, an elongated flexible insertion portion 12 which extends from the operation portion 13, and a universal cord 14 which extends from a side of the operation portion 13 and in which a light guide, a signal line, and the like are inserted. The endoscope 1 is detachably connected to a light source (not shown) as an external device, a processor (not shown) as a signal processing device, and the like, through a connector portion (not shown) provided at an end of the universal cord 14. Thus, the universal cord 14 is a connector cord that extends from the operation portion 13 and serves to connect the endoscope 1 with an external device which is utilized in combination with the endoscope 1.

The insertion portion 12 of the endoscope 1 includes a hard distal end portion 9 in which an illumination optical system, an observation optical system, and the like are arranged, a bendable portion 10 which is bendable, for example, in four direction, i.e., upward/downward/leftward/rightward, and a flexible tube portion 11 which is flexible. These portions are arranged from a distal end of the insertion portion 12 in this order. The processor outputs image signals to display an image captured by the observation optical system provided at the distal end portion 9 of the endoscope 1 on a monitor (not shown) connected thereto.

On a side surface of the operation portion 13, which also serves as a gripper of the endoscope 1, a first bending operation knob 25 and a second bending operation knob 30 are provided. The first bending operation knob 25 bends the bendable portion 10 in predetermined two directions when rotated, and the second bending operation knob 30, which shares the same rotation axis with the first bending operation knob 25, bends the bendable portion 10 in two directions each substantially perpendicular with one of the two directions in which the first bending operation knob 25 bends the bendable portion 10. Further, the operation portion 13 includes switches 17 to remotely control a video recording function of the processor, a light intensity of the light source, for example, an air/water delivery button 15, and a suction button 16, each arranged on a side of the operation portion 13. Further, the operation portion 13 includes a bending stopper 18, in which a forceps channel 18a is formed, at a side the insertion portion 12 is coupled to. In the drawings, reference character 21 indicates an upward/downward bend control lever, and reference character 22 indicates a rightward/leftward bend control lever. The operator manipulates the upward/downward bend control lever 21 and the rightward/leftward bend control lever 22 in a predetermined manner so as to control the rotation of the first bending operation knob 25 and the second bending operation knob 30, respectively.

Figure 2:
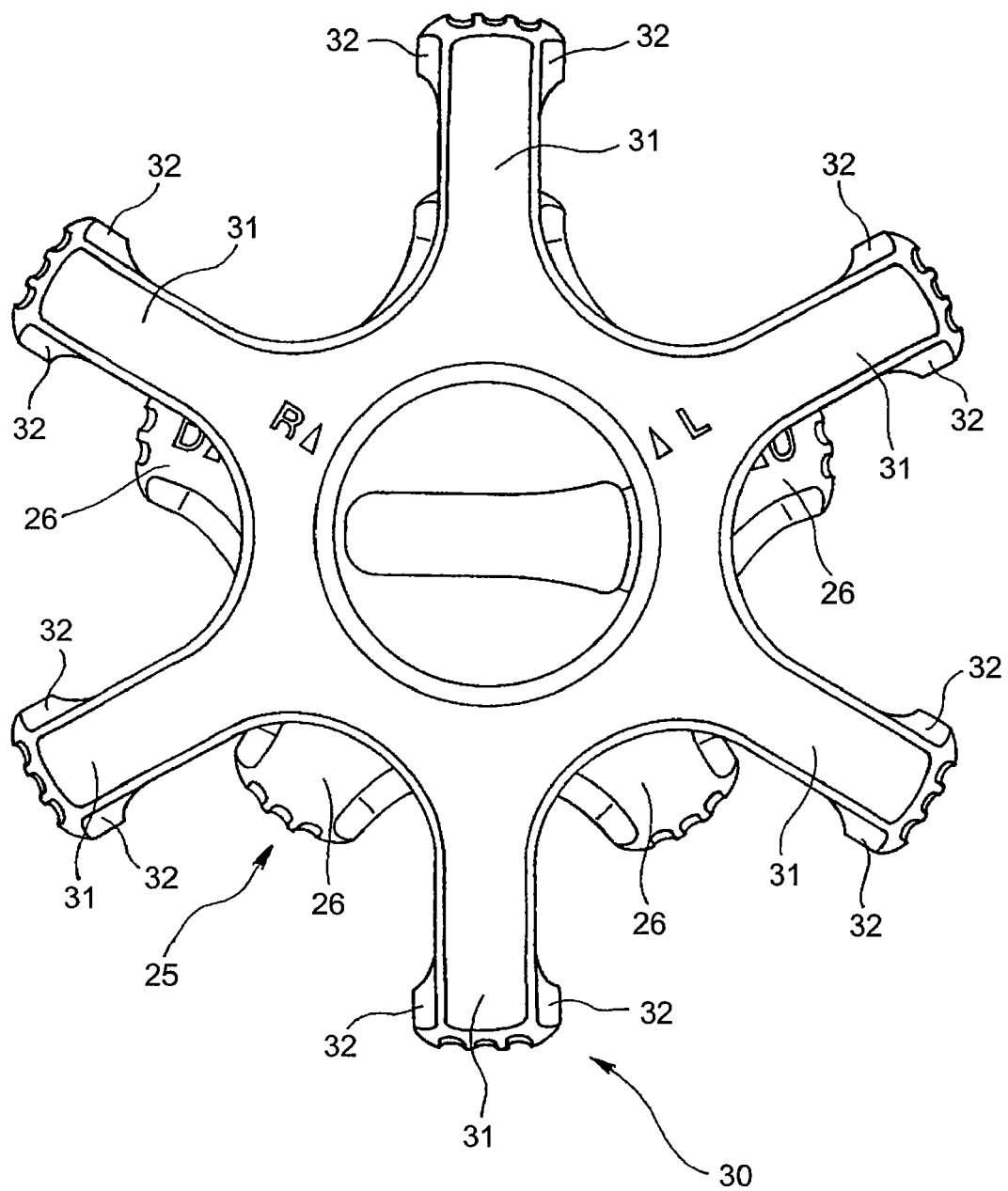
FIG. 2 schematically shows a first bending operation knob and a second bending operation knob.
Figure 3:
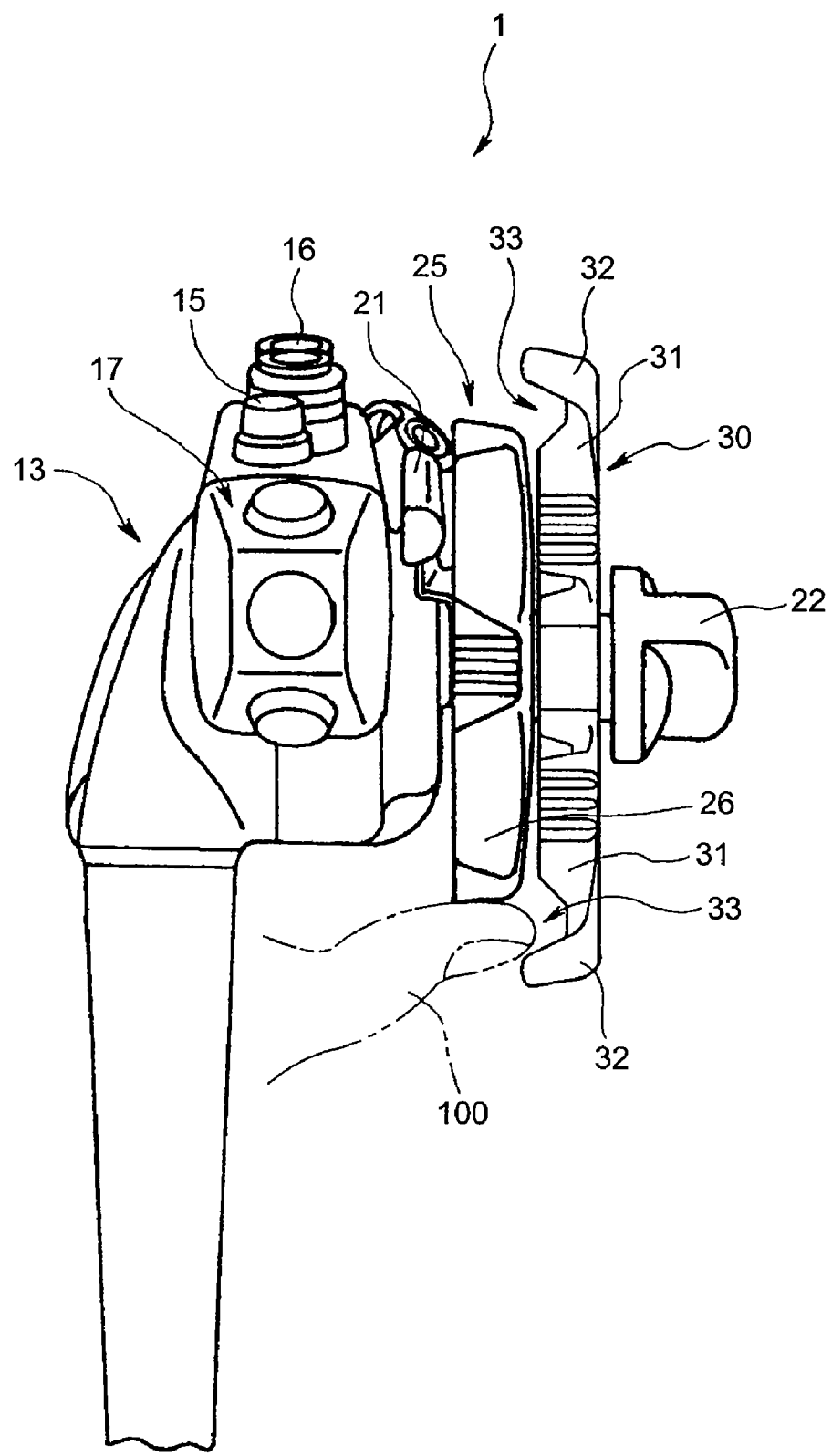
FIG. 3 is a schematic view of an operation portion of the endoscope from a side of switches.

The first bending operation knob 25 and the second bending operation knob 30 according to the first embodiment will be described in detail below with reference to FIGS. 2 and 3. FIG. 2 schematically shows the first bending operation knob 25 and the second bending operation knob 30. FIG. 3 is a top view of the operation portion 13 of FIG. 1 shown from a side of the switches 17.

As shown in FIG. 2, the first bending operation knob 25 has a substantially disk-like shape and includes plural protrusions. Specifically, the first bending operation knob 25 includes five protrusions 26 which extend radially toward an outer circumference. The first bending operation knob 25 is placed on the operation portion 13 (see FIG. 1) so that the first bending operation knob 25 can rotate around a central point of the substantially disk-like shape thereof. Five protrusions 26 each extend from a center of rotation of the first bending operation knob 25 toward the outer circumference by substantially the same amount. A farthest portion of each of the protrusions 26 from the center of rotation is a tip portion at which an outer diameter of the first bending operation knob 25 is largest.

The operator rotates the first bending operation knob 25 around the center thereof to bend the bendable portion 10 of the endoscope 1 in two directions. In the first embodiment, when the first bending operation knob 25 rotates in a clockwise direction in FIG. 2, the bendable portion 10 of the endoscope 1 is bent downward on the screen of the external monitor electrically connected to the endoscope 1. On the other hand, when the first bending operation knob 25 rotates in an anti-clockwise direction in FIG. 2, the bendable portion 10 of the endoscope 1 is bent upward on the screen of the monitor.

Further, as shown in FIG. 2, the second bending operation knob 30 has a substantially disk-like shape and includes plural protrusions that are arranged substantially equiangularly and extend radially toward an outer circumference. Specifically, the second bending operation knob 30 includes six protrusions 31. The second bending operation knob 30 can be rotated around a central point thereof and is arranged over the first bending operation knob 25 in the operation portion 13.

Six protrusions 31 extend from the center of rotation towards an outer circumference of the second bending operation knob 30 by substantially the same predetermined amount. A farthest portion of each of the six protrusions 31 from the center of rotation is a tip portion at which an outer diameter of the second bending operation knob is largest. Further, the six protrusions 31 of the second bending operation knob 30 extend farther than the five protrusions 26 of the first bending operation knob 25. In other words, the length of the protrusion 31 of the second bending operation knob 30 from the center of rotation to the tip portion of the protrusion 31 is longer than the length of the protrusion 26 of the first bending operation knob 25 from the center of rotation to the tip portion. Further, a finger stopper 32 is provided in each side of the tip portion of each of the six protrusions 31, and is projected in a direction of rotation. Here, at least one of the six protrusions 31 in the second bending operation knob 30 may be shorter than each of the five protrusions 26 of the first bending operation knob 25.

As shown in FIG. 3, each of the six protrusions 31 of the second bending operation knob 30 has a depression 33 on a surface facing the first bending operation knob 25. The depression 33 has a U-shaped section. Specifically, the depression 33 is formed on the protrusion 31 on the surface facing the first bending operation knob 25, and the depression 33 is arranged in proximity to a position corresponding to a projection of a circular orbit the tip portion of the first bending operation knob 25 passes through during rotation. In other words, when the protrusion 31 of the second bending operation knob 30 is positioned over the protrusion 26 of the first bending operation knob 25, the depression 33 formed in the protrusion 31 of the second bending operation knob 30 on the surface facing the first bending operation knob 25 is in the proximity to the tip portion of the protrusion 26 of the first bending operation knob 25, and the depression 33 runs in a direction substantially perpendicular to the direction the protrusion 31 extends from the center of rotation. In still another words, when the protrusion 31 of the second bending operation knob 30 is positioned over the protrusion 26 of the first bending operation knob 25, the surface of the protrusion 31 of the second bending operation knob 30 faces with the tip portion of the protrusion 26 of the first bending operation knob 25. The depression 33 is formed in the proximity to this surface as a groove with a U-shaped section. For example, if one pushes the tip portion of the protrusion 26 with a finger and rotates the first bending operation knob 25, the movement of the finger draws a circular orbit. If this circular orbit is projected onto the surface of the second bending operation knob 30, the projected orbit is included in the portion where the depression is formed. Therefore, with the depression 33 formed in such a position in the second bending operation knob 30, a finger of the operator rotating the first bending operation knob 25 is guided into the depression 33, and is prevented from rotating the second bending operation knob 30. The depression 33 is, for example, a groove of 20 mm in depth.

When the operator rotates the second bending operation knob 30, the bendable portion 10 of the endoscope 1 is bent in two directions, and the rotation axis of the second bending operation knob 30 is the same as the rotation axis of the first bending operation knob 25. Specifically, in the first embodiment, when the second bending operation knob 30 rotates in a clockwise direction in FIG. 2, the bendable portion 10 of the endoscope 1 is bent in a rightward direction on the screen of the monitor. On the other hand, when the second bending operation knob 30 rotates in an anti-clockwise direction, the bendable portion 10 of the endoscope 1 is bent in a leftward direction on the screen of the monitor.

Since the number of the protrusions 26 of the first bending operation knob 25 is different from the number of protrusions 31 of the second bending operation knob 30, even when one of the five protrusions 26 of the first bending operation knob 25 is positioned in the same direction as one of the six protrusions 31 of the second bending operation knob 30, at least one of the protrusions 31 of the second bending operation knob 30 is always arranged over one of the five depressions of the first bending operation knob 25.

An operation performed by the operator to rotate the first bending operation knob 25 and the second bending operation knob 30 of the operation portion 13 will be described below. Firstly, the operator grabs the operation portion 13 with one hand to rotate the first bending operation knob 25 and the second bending operation knob 30. According to the rotation of the first bending operation knob 25 and the second bending operation knob 30, the bendable portion 10 of the insertion portion 12 is bent in a desired direction. Specifically, the operator rotates the first bending operation knob 25 by pushing the tip portion of the protrusion 26 of the first bending operation knob 25 with a finger 100 as shown in FIG. 3, for example. Then, the distal end portion 9 of the endoscope 1 is bent in one of two directions, i.e., upward direction and downward direction on the screen of the monitor, according to the rotation of the first bending operation knob 25.

As shown in FIG. 3, when the protrusion 26 pushed by the finger 100 of the operator who rotates the first bending operation knob 25 overlaps with one of the protrusions 31 of the second bending operation knob 30, a tip portion of the finger 100 fits in the depression 33 of the protrusion 31, and substantially does not touch the second bending operation knob 30. Therefore, the second bending operation knob 30 does not obstruct the manipulation of the operator rotating the first bending operation knob 25, whereby the operator can rotate the first bending operation knob 25 smoothly. Though the operator is expected to push the tip portion of the protrusion 26 by a thumb in most of the cases, the operator may push the tip portion with any of the fingers.

The operator may put a finger, e.g., a middle finger, of the hand, by which the operator holds the operation portion 13, on the protrusion 31 of the second bending operation knob 30 to rotate the second bending operation knob 30. Then, the tip portion 9 of the endoscope 1 is bent in one of two directions, i.e., in rightward or leftward direction on the screen of the monitor, according to the rotation of the second bending operation knob 30. The protrusion 31 of the second bending operation knob 30 has the finger stopper 32 in the tip portion as shown in FIG. 2. Therefore, when the operator rotates the second bending operation knob 30 with a middle finger, for example, the middle finger is held and secured by the finger stopper 32 of the protrusion 31, whereby the operator can easily rotate the second bending operation knob 30. Additionally, when the operator is to manipulate the air/water delivery button 15 or the suction button 16 that are provided on a side surface of the operation portion 13 with the middle finger of the hand holding the operation portion 13, the operator may put an index finger, a medicinal finger, or a little finger on one of the six protrusions 31 of the second bending operation knob 30 to rotate the second bending operation knob 30. Specifically, the operator can flexibly bend the bendable portion 10 of the endoscope 1 by a desired amount at will by manipulating the six protrusions 31 of the second bending operation knob 30 with a preferable finger according to the required amount of rotation of the second bending operation knob 30.

Thus, the operator can easily perform the manipulation to rotate the first bending operation knob 25 and the second bending operation knob 30 with any finger of the hand holding the operation portion 13 to bend the bendable portion 10 so as to bend the bendable portion 10 and direct the distal end portion 9 of the insertion portion 12 toward a desired direction as appropriate.

As can be seen from the foregoing, according to the endoscope 1 of the first embodiment, since the length from the center of rotation of the second bending operation knob 30 to the tip portion of each of the six protrusions 31 is longer than the length from the center of rotation of the first bending operation knob 25 to the tip portion of each of the five protrusions 26, the operator can easily rotate the second bending operation knob 30 without obstructed by the presence of the protrusion 26 of the first bending operation knob 25.

Further, when the operator rotates the first bending operation knob 25 with the finger 100, the tip portion of the finger 100 substantially does not touch the second bending operation knob 30 even when the protrusion 26 which the operator pushes with the finger 100 comes directly over one of the protrusions 31 of the second bending operation knob 30. Therefore, the operator can rotate the first bending operation knob 25 smoothly without being obstructed by the presence of the second bending operation knob 30. Further, since the protrusion 31 of the second bending operation knob 30 has the finger stopper 32 at the tip portion, the operator can put the middle finger, for example, on the finger stopper 32 of the protrusion 31 while rotating the second bending operation knob 30. Thus, the middle finger is securely held, and the operator can easily rotate the second bending operation knob 30.

Thus, since the bendable portion 10 of the endoscope 1 can be bent by the simplified operation, the operator can easily direct the distal end portion of the endoscope 1 in a desired direction only with a hand holding the operation portion, and the size of the hand does not matter. Therefore, the operator can use the other hand freely. Thus, when the operator directs the distal end portion of the endoscope in a desired direction at a time the insertion portion is inserted or reaches the examined region inside the body cavity of the patient for the observation of the examined region, the operator can hold the insertion portion of the endoscope in the other hand to prevent the peristaltic motions of the large intestine or the like from pushing back the insertion portion toward the anus side. In addition, the operator can easily manipulate the pair of bending operation knobs with one hand as described above.

Figure 4:
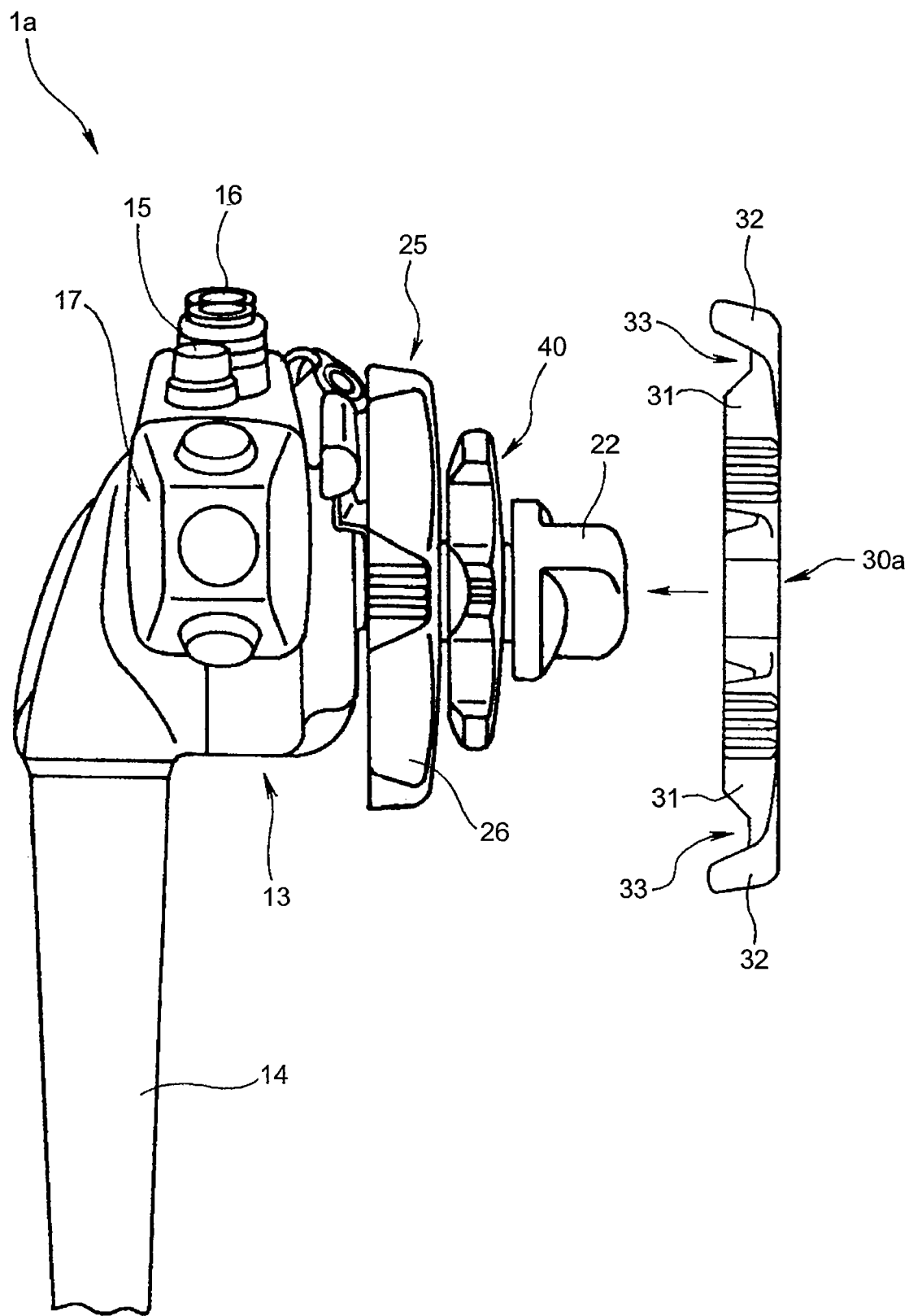
FIG. 4 is a schematic view of the operation portion of the endoscope from the side of the switches and shows how an attachment knob is arranged.
Figure 5:
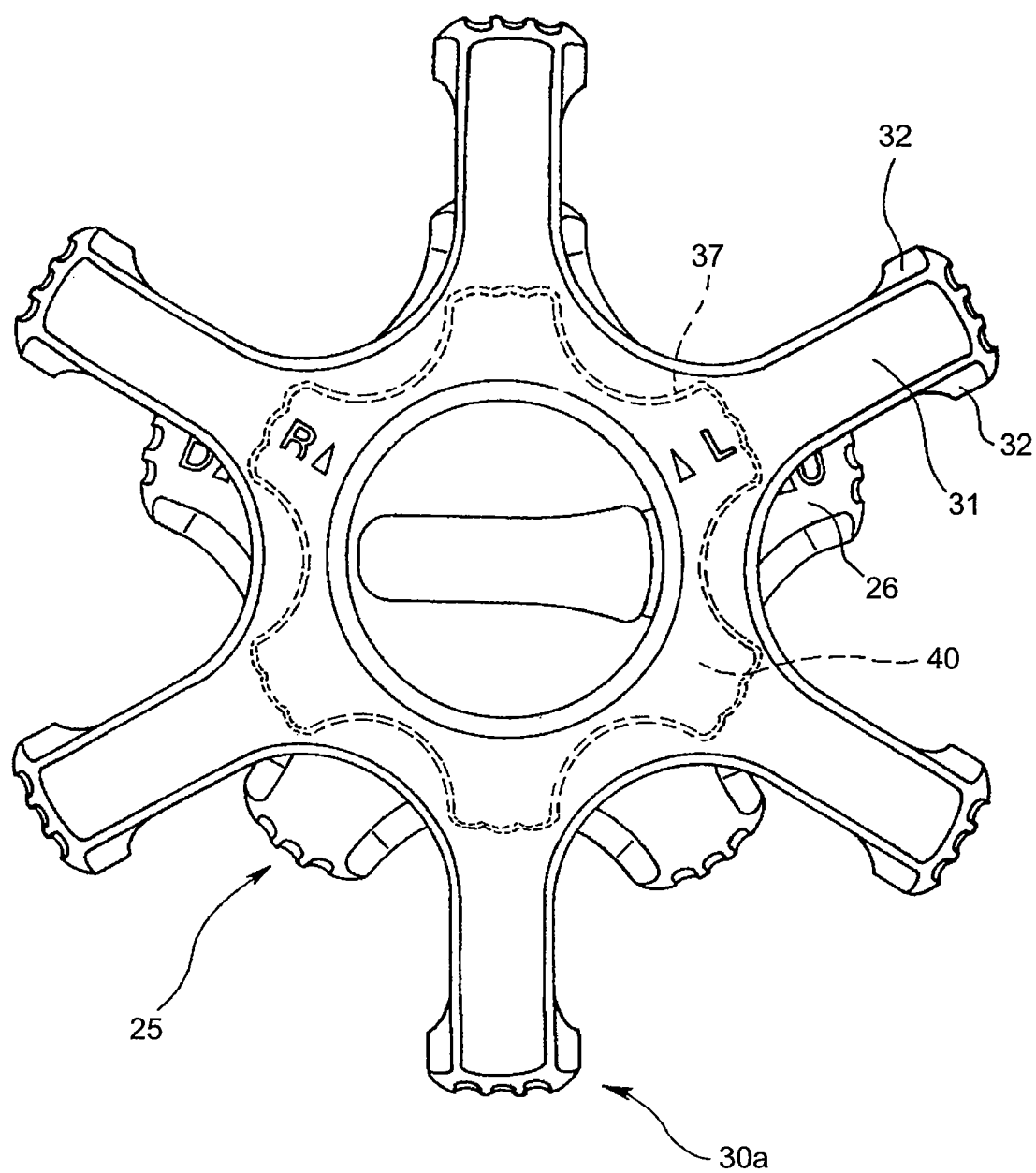
FIG. 5 schematically shows the attachment knob fit onto the second bending operation knob.

As shown in FIG. 4, an attachment knob 30a may be employed as a supportive member which is detachable from a second bending operation knob 40 of an endoscope 1a for bending operation of the endoscope. The attachment knob 30a has a protrusion 31 corresponding to the protrusion in the second bending operation knob 30 described above. Further, the attachment knob 30a has a fitting portion 37 which is a depression that has substantially the same shape as the second bending operation knob 40 as shown in FIG. 5 and serves for engagement. The second bending operation knob 40 fits into the fitting portion 37 of the attachment knob 30a thereby securing the attachment knob 30a on the second bending operation knob 40. The operator can selectively attach/detach and use the attachment knob 30a depending on the use and condition of the endoscope 1. When the attachment knob 30a is fitted onto the second bending operation knob 40 of the endoscope 1a, the endoscope 1a takes a form as the endoscope 1 shown in FIG. 4. When the second bending operation knob 40 is fitted into the attachment knob 30a, the second bending operation knob 40 works in the same manner as the second bending operation knob 30 mentioned above. Therefore, the operator can rotate the second bending operation knob 40 by rotating the attachment knob 30a fitted thereon, and thus the operator can rotate the second bending operation knob 40 in the same manner as the rotation of the second bending operation knob 30.

In the above description, the operator uses the thumb or the middle finger to rotate the first bending operation knob 25 or the second bending operation knob 30. The operator, however, may use any one of the fingers as convenient for the manipulation of the bending operation knob.

Figure 6:
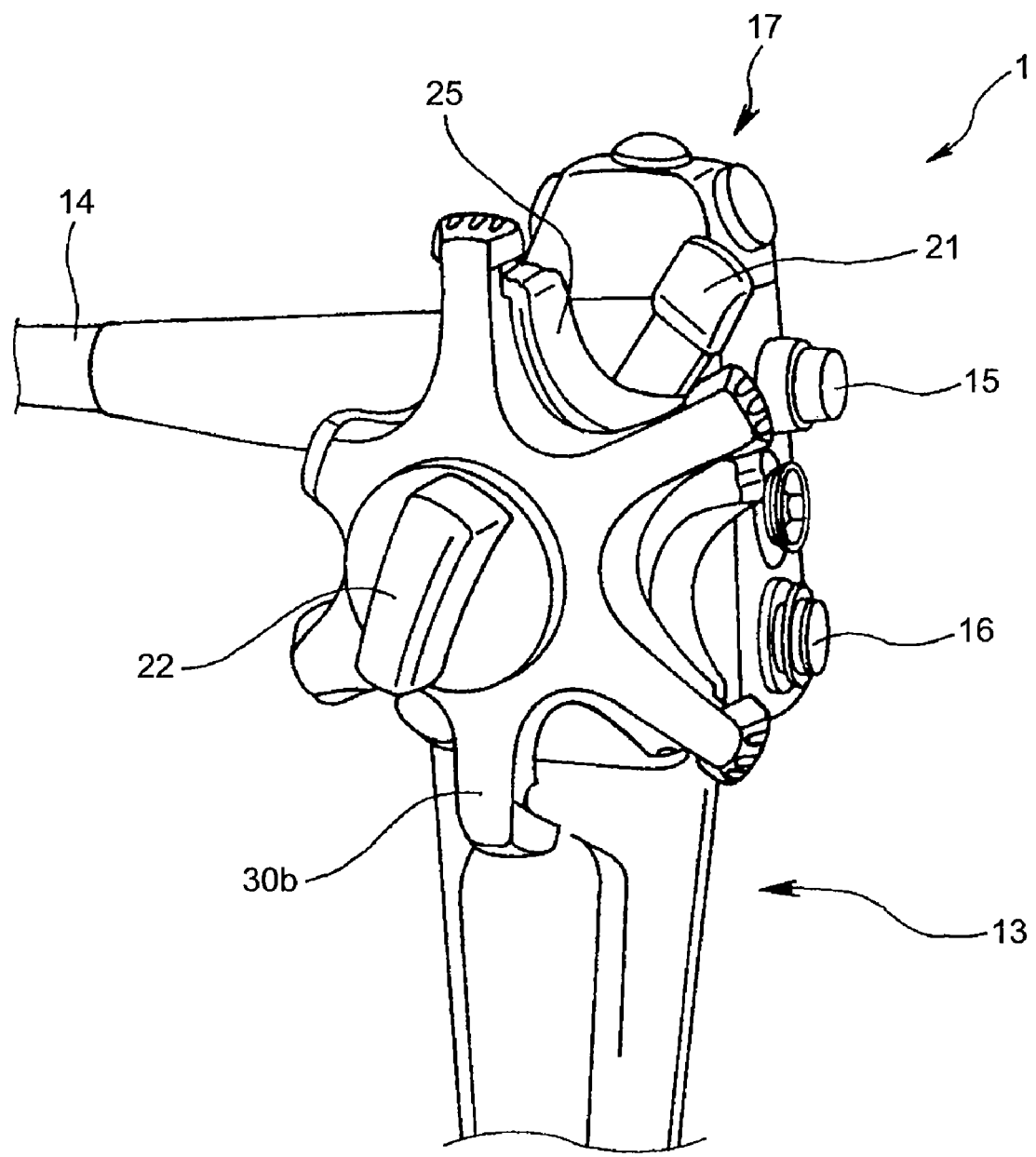
FIG. 6 shows a schematic structure of an endoscope according to a second embodiment.
Figure 7:
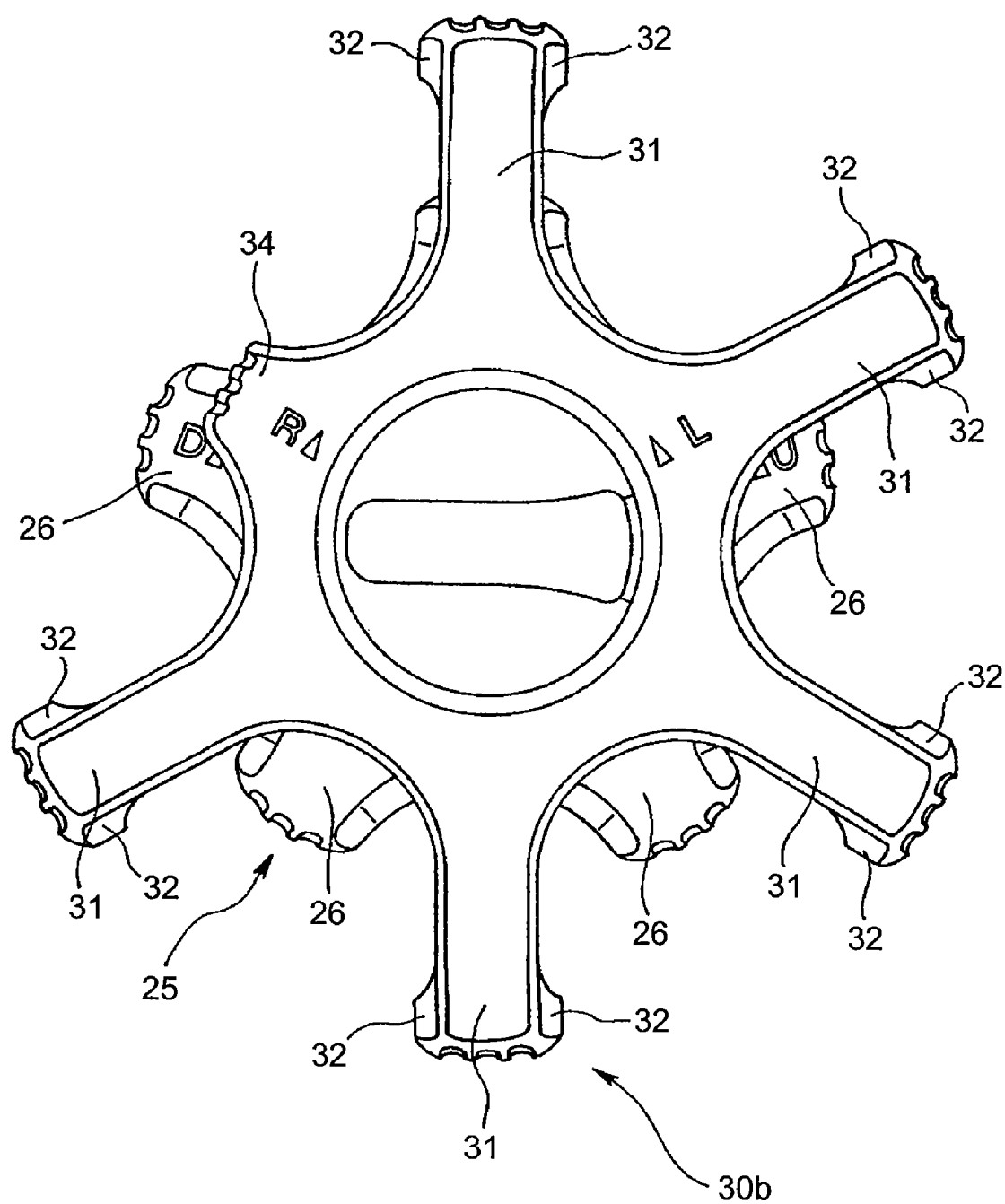
FIG. 7 schematically shows a first bending operation knob and a second bending operation knob.

A second embodiment of the present invention will be described below with reference to the accompanying drawings. The second embodiment is a modification of the endoscope 1 according to the first embodiment. The same element as in the endoscope 1 of the first embodiment will be denoted by the same reference character and the description thereof will not be repeated. FIG. 6 is a schematic view of a schematic structure of an endoscope according to the second embodiment. FIG. 7 is a schematic view of the first bending operation knob 25 and a second bending operation knob 30b.

As shown in FIG. 6 and similarly to the first embodiment, the second bending operation knob 30b has a substantially disk-like shape and has plural protrusions that radially extend to an outer circumference equiangularly. Specifically, the second bending operation knob 30b has five protrusions 31 and one protrusion 34 as shown in FIG. 7. The second bending operation knob 30b can be rotated around the central point of the disk-like shape thereof as the center of rotation, similarly to the first embodiment. The second bending operation knob 30b is arranged over the first bending operation knob 25 in the operation portion 13.

As shown in FIG. 7, the second bending operation knob 30b includes five protrusions 31 each extending from the center of rotation toward an outer circumference of the second bending operation knob 30b by substantially the same predetermined amount. Further, the second bending operation knob 30b has the protrusion 34 which is different from the five protrusions 31. The protrusion 34 extends from the center of rotation toward the outer circumference of the second bending operation knob 30b by an amount smaller than the amount of extension of each of the five protrusions 31 from the center of rotation.

Further, the amount of extension of the protrusion 34 of the second bending operation knob 30b is smaller than the amount of extension of each of the five protrusions 26 of the first bending operation knob 25. In other words, the length of the protrusion 34 from the center of rotation of the second bending operation knob 30b to the tip portion of the protrusion 34 is shorter than the length of each of the five protrusions 26 of the first bending operation knob 25 from the center of rotation to the tip portion. The number of the protrusion 34 is not limited to one. Plural protrusions 34 may be provided in the second bending operation knob 30b. The second bending operation knob 30b has at least one protrusion 31.

Similarly to the first embodiment, each of the five protrusions 31 of the second bending operation knob 30b has a depression 33, which has a U-shaped section, on a surface facing the first bending operation knob 25 as shown in FIG. 3. When the first bending operation knob 25 rotates, the tip portion of the first bending operation knob 25 follows a circular orbit. The protrusion 31 of the second bending operation knob 30b is provided with the depression 33 on the surface facing the first bending operation knob 25 in proximity to the projection of the circular orbit on the second bending operation knob 30b.

When the first bending operation knob 25 and the second bending operation knob 30b are in the position shown in FIG. 6, the protrusion 34 of the second bending operation knob 30b protrudes towards a side of the universal cord 14 which connects the endoscope 1 and the external device which is employed in combination with the endoscope 1. In the state shown in FIG. 6, the bendable portion 10 (see FIG. 1) of the endoscope 1 is substantially in a linear condition. Specifically, when the bendable portion 10 is substantially in a linear condition, the protrusion 34 of the second bending operation knob 30b is over the protrusion 26 which is positioned in front of the operator when the operator holds the operation portion 13 as shown in FIGS. 6 and 7.

Similarly to the first embodiment, the operator grabs the operation portion 13 by one hand, to rotate the first bending operation knob 25 and the second bending operation knob 30b, thereby bending the bendable portion 10 of the insertion portion 12 in a desired direction. Further, the operator grabs the operation portion 13 in such a manner that a portion connected to the universal cord 14, which serves as a connector cord, comes in front of the operator, and manipulates the endoscope 1 in various manners. During manipulations, the operator puts the thumb on the first bending operation knob 25, or pushes the first bending operation knob 25 with the thumb, for example, to rotate the first bending operation knob 25. Particularly in the first bending operation knob 25, the operator tends to push or pull the protrusion 26 at the side of the universal cord 14 by the thumb.

The operator may rotate the first bending operation knob 25 with any finger other than the thumb. The operator may choose a finger so that the operator can easily manipulate the first bending operation knob.

Since the amount of protrusion of the protrusion 34 of the second bending operation knob 30b at the side of the universal cord 14 is smaller than the amount of protrusion of the first bending operation knob 25, the operator can push or pull the protrusion 26 of the first bending operation knob 25 substantially without touching the protrusion 34 of the second bending operation knob 30b. Therefore, the operator can easily rotate the first bending operation knob 25 without being obstructed by the presence of the protrusion 34 of the second bending operation knob 30b. Thus, the operator can easily rotate the first bending operation knob 25, and easily bend the bendable portion 10 of the insertion portion 12 upward and downward on the screen of the monitor.

Thus, the second embodiment can realize the endoscope 1 which can provide advantages of the first embodiment and in which the first bending operation knob 25 can be easily rotated. Further, in the endoscope 1 according to the second embodiment, when the protrusion 34 of the second bending operation knob 30b is arranged at a predetermined reference position, for example, when the protrusion 34 is arranged so as to protrude toward the universal cord 14 as shown in FIG. 6, the bendable portion 10 can be easily arranged in a substantially linear condition. Therefore, by aligning the protrusion 34 in the reference position, the operator can easily arrange the bendable portion 10 in a substantially linear condition even when the bendable portion 10 is in the body cavity of the patient. Further, by checking the positional relation between the reference position and the protrusion 34, the operator can easily estimate a degree of bending of the bendable portion 10 inside the body cavity, for example.

The second bending operation knob 30b of the second embodiment may be an attachment-type knob (see FIGS. 4 and 5) as described in relation to the first embodiment. Further, the first bending operation knob 25 and the second bending operation knob 30, 30b of the endoscope 1 according to the first and the second embodiments may be a pair of bending operation knobs which is detachably attached to one side surface of the operation portion 13 of the endoscope 1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion portion which has a bendable portion;
an operation portion from which the insertion portion extends;
a first bending operation knob which is arranged directly on a surface of the operation portion, includes plural first protrusions, and is rotatable to bend the bendable portion in a first direction; and
a second bending operation knob which is arranged directly over the first bending operation knob, includes plural second protrusions, and is rotatable to bend the bendable portion in a second direction, such that the first bending operation knob is positioned between the surface of the operation portion and the second bending operation knob,
the first bending operation knob sharing an axis of rotation with the second bending operation knob,
wherein a length each of the plural second protrusions from a center of rotation to a tip portion of each of the plural second protrusions is longer than a length of one of the plural first protrusions from the center of rotation to a tip portion of each of the plural first protrusions, and
at least one of the plural second protrusions has a depression formed in the second protrusion of the second bending operation knob on a surface facing the first protrusion of the first bending operation knob arranged directly on the surface of the operation portion.

2. The endoscope according to claim 1, wherein
the at least one of the second protrusions has a finger stopper which is provided in the tip portion of the second protrusions, the finger stopper protruding in a direction of rotation.

3. An endoscope comprising:
an insertion portion which has a bendable portion;
an operation portion from which the insertion portion extends;
a first bending operation knob which is arranged on a surface of the operation portion, includes plural first protrusions, and is rotatable to bend the bendable portion in a first direction; and
a second bending operation knob which is arranged over the first bending operation knob, includes plural second protrusions, and is rotatable to bend the bendable portion in a second direction,
the first bending operation knob sharing an axis of rotation with the second bending operation knob,
wherein a length of at least one of the plural second protrusions from a center of rotation to a tip portion of one of the plural second protrusions is longer than a length of one of the plural first protrusions from the center of rotation to tip portions of the plural first protrusions, and
at least one of the plural second protrusions has a depression formed in the second protrusion of the second bending operation knob on a surface facing the first bending operation knob when the second protrusion of the second bending operation knob is positioned over the first protrusion of the first bending operation knob arranged on the surface of the operation portion, and
of the plural second protrusions, remaining second protrusions other than the at least one of the second protrusions is shorter than each of the plural first protrusions in length from the center of rotation to each tip portion of the first protrusions.

4. The endoscope according to claim 3, wherein the remaining second protrusions is arranged so as to protrude toward a side of a connector cord, when the bendable portion becomes substantially linear during rotation, the connector cord extending from the operation portion and connecting the endoscope with an external device, the external device being used in combination with the endoscope.

5. An endoscope comprising:

an insertion portion which has a bendable portion;

an operation portion from which the insertion portion extends;

a first bending operation knob which is arranged directly on a surface of the operation portion, includes plural first protrusions, and is rotatable to bend the bendable portion in a first direction; and a second bending operation knob which is arranged directly over the first bending operation knob, includes plural second protrusions, and is rotatable to bend the bendable portion in a second direction, such that the first bending operation knob is positioned between the surface of the operation portion and the second bending operation knob, the first bending operation knob sharing an axis of rotation with the second bending operation knob, wherein a length of each of the plural second protrusions from a center of rotation to a tip portion of each of the plural second protrusions is longer than a length of each of the plural first protrusions from the center of rotation to tip portions of each of the plural first protrusions, at least one of the plural second protrusions has a depression formed in the second protrusion of the second bending operation knob on a surface facing the first bending operation knob arranged directly on the surface of the operation portion, and said depression is configured to permit an operator's finger to be guided into the depression such as to avoid rotating the second bending operation knob while the first protrusion of the first bending operation knob is pushed by same finger to operate the first bending operation knob and overlaps with the second protrusion of the second bending operation knob.

* * * * *